United States Patent
Kishida et al.

(10) Patent No.: US 9,624,144 B2
(45) Date of Patent: Apr. 18, 2017

(54) 1,3-BUTADIENE-SEPARATING MATERIAL, AND SEPARATION METHOD USING SAID SEPARATING MATERIAL

(71) Applicant: SHOWA DENKO K.K., Tokyo (JP)

(72) Inventors: Keisuke Kishida, Oita (JP); Yoshihiro Watanabe, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 217 days.

(21) Appl. No.: 14/428,425

(22) PCT Filed: Sep. 11, 2013

(86) PCT No.: PCT/JP2013/074537
§ 371 (c)(1),
(2) Date: Mar. 16, 2015

(87) PCT Pub. No.: WO2014/045967
PCT Pub. Date: Mar. 27, 2014

(65) Prior Publication Data
US 2015/0232397 A1    Aug. 20, 2015

(30) Foreign Application Priority Data
Sep. 18, 2012    (JP) ................ 2012-204852

(51) Int. Cl.
C07C 7/12          (2006.01)
B01D 53/047    (2006.01)
(Continued)

(52) U.S. Cl.
CPC ............. C07C 7/12 (2013.01); B01D 53/047 (2013.01); B01D 53/0462 (2013.01);
(Continued)

(58) Field of Classification Search
None
See application file for complete search history.

(56) References Cited

U.S. PATENT DOCUMENTS 3,992,471 A    11/1976    Priegnitz
4,567,309 A    1/1986    Kulprathipanja
(Continued)

FOREIGN PATENT DOCUMENTS

JP    51-43702 A    4/1976
JP    62-169734 A    7/1987
(Continued)

OTHER PUBLICATIONS

Kazuhiro Uemura et al., "Mirai Zairyo (Expected Materials for the Future)", 2002, pp. 44-51, vol. 2, No. 12.
(Continued)

*Primary Examiner* — Tam M Nguyen
(74) *Attorney, Agent, or Firm* — Sughrue Mion, PLLC (57) ABSTRACT

The invention separating material and separation method make it possible to separate and collect 1,3-butadiene selectively from a mixed gas containing 1,3-butadiene and a $C_4$ hydrocarbon other than 1,3-butadiene. A separating material capable of adsorbing 1,3-butadiene selectively includes: a dicarboxylic acid compound (I) represented by formula (I) (wherein $R^1$, $R^2$, $R^3$ and $R^4$ independently represent a hydrogen atom, an alkyl group or the like); a metal ion such as a zinc ion and a cobalt ion; and a metal complex having such a structure that multiple pseudo-diamondoid frameworks are intruded mutually, wherein each of the pseudo-diamondoid frameworks comprises an organic ligand (II) that is represented by formula (II) (wherein X represents $-CH_2-$, $-CH_2-CH_2-$, $-CH=CH-$ or the like; and $R^5$, $R^6$, $R^7$, $R^8$, $R^9$, $R^{10}$, $R^{11}$ and $R^{12}$ independently represent a hydrogen atom, an alkyl group or the like) and is capable of being bidentately coordinated with the metal ion.

14 Claims, 6 Drawing Sheets

(51) Int. Cl.

| | | |
|---|---|---|
| B01D 69/10 | (2006.01) | |
| B01D 71/64 | (2006.01) | |
| B01D 53/22 | (2006.01) | |
| B01D 71/38 | (2006.01) | |
| B01D 53/04 | (2006.01) | |
| C07F 3/06 | (2006.01) | |
| C07C 7/00 | (2006.01) | |
| C07F 15/02 | (2006.01) | |
| C07F 15/06 | (2006.01) | |
| B01J 20/22 | (2006.01) | |

(52) U.S. Cl.
CPC .......... *B01D 53/228* (2013.01); *B01D 69/10* (2013.01); *B01D 71/38* (2013.01); *B01D 71/64* (2013.01); *B01J 20/223* (2013.01); *C07C 7/005* (2013.01); *C07F 3/06* (2013.01); *C07F 15/02* (2013.01); *C07F 15/06* (2013.01); *B01D 2253/112* (2013.01); *B01D 2253/20* (2013.01); *B01D 2256/24* (2013.01); *B01D 2325/12* (2013.01)

(56) References Cited

U.S. PATENT DOCUMENTS

| | | | | |
|---|---|---|---|---|
| 2014/0107333 | A1* | 4/2014 | Ma | C07D 487/22 540/145 |
| 2015/0034500 | A1* | 2/2015 | Kim | B01J 20/226 206/0.7 |
| 2015/0165415 | A1* | 6/2015 | Inubushi | F17C 11/005 546/2 |
| 2015/0329563 | A1* | 11/2015 | Kishida | B01D 53/02 95/50 |
| 2016/0159712 | A1* | 6/2016 | Kishida | B01D 53/0462 96/14 |
| 2016/0159823 | A1* | 6/2016 | Kishida | B01J 20/226 585/830 |
| 2016/0175810 | A1* | 6/2016 | Watanabe | B01J 20/2803 502/402 |
| 2016/0346759 | A1* | 12/2016 | Zhou | B01J 20/226 |

FOREIGN PATENT DOCUMENTS

| | | |
|---|---|---|
| JP | 2012-031161 A | 2/2012 |
| JP | 2013-107826 A | 6/2013 |
| JP | 2013-216622 A | 10/2013 |

OTHER PUBLICATIONS

Ryotaro Matsuda et al., "PETROTECH", 2003, pp. 97-104, vol. 26.

Satoshi Horike et al., "Dense Coordination Network Capable of Selective CO2 Capture from C1 and C2 Hydrocarbons", Journal of the American Chemical Society (JACS), 2012, pp. 9852-9855, vol. 134, No. 24.

International Search Report for PCT/JP2013/074537 dated Nov. 5, 2013.

* cited by examiner

1,3-BUTADIENE-SEPARATING MATERIAL, AND SEPARATION METHOD USING SAID SEPARATING MATERIAL

CROSS REFERENCE TO RELATED APPLICATIONS

This application is a National Stage of International Application No. PCT/JP2013/074537 filed Sep. 11, 2013 (claiming priority based on Japanese Patent Application No. 2012-204852, filed Sep. 18, 2012), the contents of which are incorporated herein by reference in their entirety.

TECHNICAL FIELD

The present invention relates to a 1,3-butadiene-separating material containing a metal complex, and a method for separating 1,3-butadiene from a mixed gas using the separating material.

BACKGROUND ART

Separating and recovering only the objective hydrocarbon gas from a mixed gas containing hydrocarbons has been known in the art.

An example of a hydrocarbon gas to be separated and recovered is 1,3-butadiene. 1,3-Butadiene is a useful compound, for example, as a starting material for the production of a synthetic rubber, and also an intermediate of large number of compounds. Commonly, 1,3-butadiene is produced by naphtha cracking or dehydrogenation of butenes. According to these productions methods, 1,3-butadiene is obtained as one component of a mixed gas. Therefore, it is necessary to selectively separate and recover 1,3-butadiene from the gas mixture. Examples of the main component having 4 carbon atoms in the product include 1,3-butadiene, isobutene, 1-butene, 2-butene, normal butane, and isobutane. Since these compounds have the same carbon number and the similar boiling point, it is difficult to separate them by an industrially employed distillation method.

An example of one of other separating methods is an extractive distillation method. This method is an absorption method using a polar solvent, and thus too much energy is used to separate 1,3-butadiene from the polar solvent. Therefore, separation by an adsorption method is desired as a method for separating and recovering 1,3-butadiene in an energy-saving manner.

However, a conventional porous material (Patent Literature 1) requires separating in a multi-stage because of poor separation performance of 1,3-butadiene, thus failing to avoid upsizing of a separation apparatus.

There has been developed, as an adsorption material capable of achieving more excellent separation performance than that of a conventional porous material, a porous metal complex which causes dynamic structural change due to external stimulation (Non-Patent Literatures 1 and 2). When using this porous material as a gas adsorption material, it has been observed that there is a particular characteristic in which gas is not adsorbed below a certain pressure, but gas adsorption occurs above a certain pressure. In addition, it has been observed that there is a characteristic in which an adsorption initiation pressure varies depending on the type of a gas subjected to adsorption.

Applying this porous material to, for example, an adsorption material in a gas separating apparatus of a pressure swing adsorption system enables gas separation with excellent efficiency. It also enables narrowing of a swing width of the pressure, which leads to the energy saving. Because of its contribution to miniaturization of the gas separating apparatus, it enables not only the enhancement of cost competitiveness in the case of selling a highly pure gas as the product, but also the reduction in cost required for equipment which needs a highly pure gas even when the highly pure gas is captively consumed inside a factory, thus eventually having the effect of reducing production cost of the final product.

There are disclosed metal complexes [Zn(R-ip)(bpe)] (R=H, Me, $NO_2$, I) composed of zinc ions, various isophthalic acid derivatives, and 1,2-di(4-pyridyl)ethylene (Patent Literature 2, and Non-Patent Literature 3). Although the study focused on adsorption and separation of a gas mixture containing hydrocarbons having 2 carbon atoms, no study have carried out in terms of adsorption and separation of a gas mixture containing hydrocarbons having 4 carbon atoms, which includes 1,3-butadiene.

CITATION LIST

Patent Literature

[Patent Literature 1]
  Japanese unexamined patent publication (Kokai) No. 51-43702
[Patent Literature 2]
  Japanese unexamined patent publication (Kokai) No. 2012-031161

Non-Patent Literature

[Non-Patent Literature 1]
  Kazuhiro Uemura, and Susumu Kitagawa, Mirai Zairyo (Expected Materials for the Future), Vol. 2, pp. 44-51 (2002)
[Non-Patent Literature 2]
  Ryotaro Matsuda, and Susumu Kitagawa, PETROTECH, Vol. 26, pp. 97-104 (2003)
[Non-Patent Literature 3]
  Satoshi Horike, Keisuke Kishida, Yoshihiro Watanabe, Yasutaka Inubushi, Daiki Umeyama, Masayuki Sugimoto, Tomohiro Fukushima, Munehiro Inukai, and Susumu Kitagawa, Journal of American Chemical Society, Vol. 134, pp. 9852-9855 (2012)

SUMMARY OF THE INVENTION

Problems to be Solved by the Invention

An object of the present invention is to provide a separating material and a separating method, which are more excellent than the prior art, capable of selectively separating and recovering 1,3-butadiene from a mixed gas containing 1,3-butadiene and a hydrocarbon having 4 carbon atoms other than 1,3-butadiene.

Means to Solve the Problems

The present inventors have intensively studied and found that the above object can be achieved by using, as a separating material, a metal complex having a structure in which pseudo-diamondoid frameworks are multiply interpenetrated, leading to the present invention. Thus, present invention includes the following embodiments [1] to [13].
[1] A 1,3-butadiene-separating material capable of selectively adsorbing 1,3-butadiene from a mixed gas containing 1,3-butadiene and a hydrocarbon having 4 carbon atoms other than 1,3-butadiene, comprising a metal complex having a structure in which pseudo-diamondoid frameworks are multiply interpenetrated, the metal complex being composed of a dicarboxylic acid compound (I) represented by the following general formula (I):

wherein $R^1$, $R^2$, $R^3$, and $R^4$ may be the same or different and represent a hydrogen atom, an alkyl group having 1 to 4 carbon atoms which may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkylamino group having 1 to 4 carbon atoms, a dialkylamino group having 2 to 4 carbon atoms, an acylamino group having 2 to 4 carbon atoms, or a halogen atom;

ions of at least one metal selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium; and an organic ligand (II), which is capable of bidentate coordination to the metal ions, represented by the following general formula (II):

wherein X represents —$CH_2$—, —$CH_2$—$CH_2$—, —CH=CH—, —C≡C—, —O—, —S—, —S—S—, —N=N—, or —NHCO—, and $R^5$, $R^6$, $R^7$, $R^8$, $R^9$, $R^{10}$, $R^{11}$, and $R^{12}$ may be the same or different and represent a hydrogen atom, an alkyl group having 1 to 4 carbon atoms which may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkylamino group having 1 to 4 carbon atoms, a dialkylamino group having 2 to 4 carbon atoms, an acylamino group having 2 to 4 carbon atoms, or a halogen atom.

[2] The 1,3-butadiene-separating material according to [1], wherein the ions of the metal are zinc ions.

[3] The 1,3-butadiene-separating material according to [1] or [2], wherein the organic ligand (II) represented by the general formula (II) is 1,2-di(4-pyridyl)ethene in which all of $R^5$, $R^6$, $R^7$, $R^8$, $R^9$, $R^{10}$, $R^{11}$, and $R^{12}$ are hydrogen atoms, and X is —CH=CH—.

[4] The 1,3-butadiene-separating material according to any one of [1] to [3], wherein, in the dicarboxylic acid compound (I) represented by the general formula (I), $R^1$, $R^3$, and $R^4$ are hydrogen atoms, and $R^2$ is a hydrogen atom, a methyl group, or a nitro group.

[5] The 1,3-butadiene-separating material according to any one of [1] to [4], wherein the metal complex has a structure in which pseudo-diamondoid frameworks are triply interpenetrated.

[6] The 1,3-butadiene-separating material according to any one of [1] to [5], wherein the hydrocarbon having 4 carbon atoms other than 1,3-butadiene is butene or butane.

[7] A separating method of 1,3-butadiene in which 1,3-butadiene is separated from a mixed gas, the method comprising an adsorption step of bringing the mixed gas containing 1,3-butadiene and a hydrocarbon having 4 carbon atoms other than 1,3-butadiene into contact with a separating material to allow the separating material to selectively adsorb 1,3-butadiene; and a regeneration step of desorbing 1,3-butadiene adsorbed onto the separating material from the separating material, and collecting 1,3-butadiene thus desorbed; wherein the separating material is the 1,3-butadiene-separating material according to any one of [1] to [6].

[8] The separating method of 1,3-butadiene according to [7], wherein the hydrocarbon having 4 carbon atoms other than 1,3-butadiene is butene or butane.

[9] The separating method of 1,3-butadiene according to [7] or [8], wherein the separating method is a pressure swing adsorption method.

[10] The separating method of 1,3-butadiene according to [7] or [8], wherein the separating method is a temperature swing adsorption method.

[11] A 1,3-butadiene-separating membrane comprising a porous support, and the 1,3-butadiene-separating material according to any one of [1] to [6] deposited on a surface portion of the porous support.

[12] A 1,3-butadiene-separating membrane comprising a polymer material, and the 1,3-butadiene-separating material according to any one of [1] to [6] kneaded with and dispersed in the polymer material.

[13] A separating method of 1,3-butadiene in which a gas having a higher 1,3-butadiene concentration than that of a mixed gas is obtained, the method comprising bringing a mixed gas containing 1,3-butadiene and a hydrocarbon having 4 carbon atoms other than 1,3-butadiene into contact with a separating membrane to selectively permeate 1,3-butadiene through the separating membrane, wherein the separating membrane is the 1,3-butadiene-separating membrane according to [11] or [12].

Effects of the Invention

According to the present invention, it is possible to separate and recover 1,3-butadiene from a mixed gas containing 1,3-butadiene with higher separation performance than that of the prior art.

The aforementioned description is not to be construed as a disclosure of all embodiments of the present invention and all advantages of the present invention.

MODE FOR CARRYING OUT THE INVENTION

The present invention will be described in more detail for the purpose of illustrating typical embodiments of the present invention, but the present invention is not limited to the following embodiments.

<Separating Material>

The 1,3-butadiene-separating material of the present invention comprises a metal complex composed of a dicarboxylic acid compound (I), specific metal ions, and an organic ligand (II), which is capable of bidentate coordination to the metal ions.

<Dicarboxylic Acid Compound (I)>

The dicarboxylic acid compound (I) used in the present invention is represented by the following general formula (I):

(I)

wherein $R^1$, $R^2$, $R^3$, and $R^4$ may be the same or different and represent a hydrogen atom, an alkyl group having 1 to 4 carbon atoms which may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkylamino group having 1 to 4 carbon atoms, a dialkylamino group having 2 to 4 carbon atoms, an acylamino group having 2 to 4 carbon atoms, or a halogen atom.

Examples of the alkyl group having 1 to 4 carbon atoms include linear or branched alkyl groups, such as a methyl group, an ethyl group, an n-propyl group, an isopropyl group, an n-butyl group, an isobutyl group, and a tert-butyl group. Examples of the substituent which may be included in the alkyl group include an alkoxy group (a methoxy group, an ethoxy group, an n-propoxy group, an isopropoxy group, an n-butoxy group, an isobutoxy group, a tert-butoxy group, etc.), an amino group, a monoalkylamino group (a methylamino group, etc.), a dialkylamino group (a dimethylamino group, etc.), a formyl group, an epoxy group, an acyloxy group (an acetoxy group, an n-propanoyloxy group, an n-butanoyloxy group, a pivaloyloxy group, a benzoyloxy group, etc.), an alkoxycarbonyl group (a methoxycarbonyl group, an ethoxycarbonyl group, an n-butoxycarbonyl group, etc.), a carboxylic anhydride group (—CO—O—CO—R group) (R is an alkyl group having 1 to 4 carbon atoms), and the like. When the alkyl group has a substituent, the number of the substituent is preferably 1 to 3, and more preferably 1.

Examples of the alkenyl group having 2 to 4 carbon atoms include a vinyl group, an allyl group, a 1-propenyl group, and a butenyl group.

Examples of the alkoxy group having 1 to 4 carbon atoms include a methoxy group, an ethoxy group, an n-propoxy group, an isopropoxy group, an n-butoxy group, an isobutoxy group, and a tert-butoxy group.

Examples of the acyloxy group having 2 to 10 carbon atoms include an acetoxy group, an n-propanoyloxy group, an n-butanoyloxy group, a pivaloyloxy group, and a benzoyloxy group.

Examples of the alkoxycarbonyl group having 2 to 4 carbon atoms include a methoxycarbonyl group, an ethoxycarbonyl group, and an n-butoxycarbonyl group.

Examples of the monoalkylamino group having 1 to 4 carbon atoms include a methylamino group. Examples of the dialkylamino group having 2 to 4 carbon atoms include a dimethylamino group. Examples of the acylamino group having 2 to 4 carbon atoms include an acetylamino group.

Examples of the halogen atom include fluorine, chlorine, bromine, and iodine atoms.

From the viewpoint of ease of taking a pseudo-diamondoid structure, $R^1$, $R^3$, and $R^4$ preferably represent a hydrogen atom or an alkyl group having 1 to 4 carbon atoms, and more preferably a hydrogen atom. $R^2$ is preferably a hydrogen atom, a methyl group, or a nitro group.

The dicarboxylic acid compound (I) is preferably isophthalic acid, 5-methylisophthalic acid, or 5-nitroisophthalic acid in which $R^1$, $R^3$, and $R^4$ are hydrogen atoms and $R^2$ is a hydrogen atom, a methyl group, or a nitro group, and more preferably 5-nitroisophthalic acid.

<Metal Ions>

Metal ions composing the metal complex used in the separating material of the present invention are ions of at least one metal selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium. Among these ions, zinc and cobalt ions are preferable, and zinc ions are more preferable, in view of gas adsorption performance.

In the case of producing the metal complex used in the separating material of the present invention, salts of the metal can be used. As the salts of the metal, a single metal salt is preferably used alone; however, two or more metal salts may be used in combination. As these metal salts, organic acid salts, such as acetate and formate; and inorganic acid salts, such as hydrochloride, hydrobromide, sulfate, nitrate, and carbonate, may be used.

<Organic Ligand (II) Capable of Bidentate Coordination>

The organic ligand (II), which is capable of bidentate coordination to metal ions, used in the present invention is represented by the following general formula (II):

(II)

wherein X is —$CH_2$—, —$CH_2$—$CH_2$—, —CH=CH—, —C≡C—, —O—, —S—, —S—S—, —N=N—, or —NHCO—, and $R^5$, $R^6$, $R^7$, $R^8$, $R^9$, $R^{10}$, $R^{11}$, and $R^{12}$ may be the same or different and represent a hydrogen atom, an alkyl group having 1 to 4 carbon atoms which may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkylamino group having 1 to 4 carbon atoms, a dialkylamino group having 2 to 4 carbon atoms, an acylamino group having 2 to 4 carbon atoms, or a halogen atom. The organic ligand capable of bidentate coordination herein means a ligand having two sites which coordinate to metal via the unshared electron pair.

X is —$CH_2$—, —$CH_2$—$CH_2$—, —CH=CH—, —C≡C—, —O—, —S—, —S—S—, —N=N—, or —NHCO—. Among these, —$CH_2$—$CH_2$—, —CH=CH—, and —NHCO— are preferable, and —CH=CH— is more preferably, since it is easy to form pseudo-diamondoid frameworks. —CH=CH— preferably has a trans structure.

Examples of the alkyl group having 1 to 4 carbon atoms include linear or branched alkyl groups, such as a methyl group, an ethyl group, an n-propyl group, an isopropyl group, an n-butyl group, an isobutyl group, and a tert-butyl group. Examples of the substituent which may be included in the alkyl group include an alkoxy group (a methoxy group, an ethoxy group, an n-propoxy group, an isopropoxy group, an n-butoxy group, an isobutoxy group, a tert-butoxy group, etc.), an amino group, a monoalkylamino group (a methylamino group, etc.), a dialkylamino group (a dimethylamino group, etc.), a formyl group, an epoxy group, an acyloxy group (an acetoxy group, an n-propanoyloxy group, an n-butanoyloxy group, a pivaloyloxy group, a benzoyloxy group, etc.), an alkoxycarbonyl group (a methoxycarbonyl group, an ethoxycarbonyl group, an n-butoxycarbonyl group, etc.), a carboxylic anhydride group (—CO—O—CO—R group) (R is an alkyl group having 1 to 4 carbon atoms), and the like. When the alkyl group has a substituent, the number of the substituent is preferably 1 to 3, and more preferably 1.

Examples of the alkenyl group having 2 to 4 carbon atoms include a vinyl group, an allyl group, a 1-propenyl group, and a butenyl group.

Examples of the alkoxy group having 1 to 4 carbon atoms include a methoxy group, an ethoxy group, an n-propoxy group, an isopropoxy group, an n-butoxy group, an isobutoxy group, and a tert-butoxy group.

Examples of the acyloxy group having 2 to 10 carbon atoms include an acetoxy group, an n-propanoyloxy group, an n-butanoyloxy group, a pivaloyloxy group, and a benzoyloxy group.

Examples of the alkoxycarbonyl group having 2 to 4 carbon include a methoxycarbonyl group, an ethoxycarbonyl group, and an n-butoxycarbonyl group.

Examples of the monoalkylamino group having 1 to 4 carbon atoms include a methylamino group. Examples of the dialkylamino group having 2 to 4 carbon atoms include a dimethylamino group. Examples of the acylamino group having 2 to 4 carbon atoms include an acetylamino group.

Examples of the halogen atom include fluorine, chlorine, bromine, and iodine atoms.

$R^5$, $R^6$, $R^7$, $R^8$, $R^9$, $R^{10}$, $R^{11}$, and $R^{12}$ are preferably hydrogen atoms or alkyl groups having 1 to 4 carbon atoms which have no substituent in view of gas adsorption amount, and more preferably, all of $R^5$, $R^6$, $R^7$, $R^8$, $R^9$, $R^{10}$, $R^{11}$, and $R^{12}$ are hydrogen atoms.

The organic ligand (II), which is capable of bidentate coordination, is preferably 1,2-di(4-pyridyl)ethene in which all of $R^5$, $R^6$, $R^7$, $R^8$, $R^9$, $R^{10}$, $R^{11}$, and $R^{12}$ are hydrogen atoms and X is —CH=CH—.

<Production Method>

The metal complex having a structure in which pseudo-diamondoid frameworks are multiply interpenetrated used in the separating material of the present invention can be produced by reacting a dicarboxylic acid compound (I), a salt of at least one metal selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium, and an organic ligand (II) capable of bidentate coordination to ions of the metal under normal pressure in a solvent for several hours to several days to precipitate a crystal. The metal complex of the present invention can be obtained, for example, by mixing an aqueous solution or aqueous-organic solvent solution of the metal salt with an organic solvent solution containing a dicarboxylic acid compound (I) and an organic ligand (II) capable of bidentate coordination under normal pressure, and reacting the mixture.

A mixing ratio of the dicarboxylic acid compound (I) to the organic ligand (II) capable of bidentate coordination in the production of a metal complex is preferably a molar ratio of dicarboxylic acid compound (I):organic ligand (II) capable of bidentate coordination within a range of 1:5 to 8:1, and more preferably 1:3 to 6:1. Even if the reaction is carried out in the molar ratio which does not fall within the above range, the objective metal complex can be obtained. However, this is not preferable since the yield decreases and the side reaction also increases.

A mixing ratio of the metal salt to the organic ligand (II) capable of bidentate coordination in the production of a metal complex is preferably a molar ratio of metal salt:organic ligand (II) capable of bidentate coordination within a range of 3:1 to 1:3, and more preferably 2:1 to 1:2 When the molar ratio does not fall within the above range, the yield of the objective metal complex may decrease, and it may also be difficult to purify the obtained metal complex since the unreacted raw material remains.

The molar concentration of the dicarboxylic acid compound (I) in the solution for the production of the metal complex is preferably within a range of 0.005 to 5.0 mol/L, and more preferably 0.01 to 2.0 mol/L. Even if the reaction is carried out in the lower concentration, the objective metal complex can be obtained. However, this is not preferable since the yield decreases. When the reaction is carried out in the higher concentration, solubility may decrease and thus the reaction may not proceed smoothly.

The molar concentration of the metal salt in the solution for the production of the metal complex is preferably within a range of 0.005 to 5.0 mol/L, and more preferably 0.01 to 2.0 mol/L. Even if the reaction is carried out in the lower concentration, the objective metal complex can be obtained. However, this is not preferable since the yield decreases. When the reaction is carried out in the higher concentration, the unreacted metal salt may remain and thus it may be difficult to purify the obtained metal complex.

The molar concentration of the organic ligand (II) capable of bidentate coordination in the solution for the production of the metal complex is preferably within a range of 0.001 to 5.0 mol/L, and more preferably 0.005 to 2.0 mol/L. Even if the reaction is carried out in the lower concentration, the objective metal complex can be obtained. However, this is not preferable since the yield decreases. When the reaction is carried out in the higher concentration, solubility may decrease and thus the reaction may not proceed smoothly.

<Solvent>

As the solvent used in the production of the metal complex, an organic solvent, water, or a mixed solvent thereof may be used. Specifically, methanol, ethanol, propanol, diethylether, dimethoxyethane, tetrahydrofuran, hexane, cyclohexane, heptane, benzene, toluene, methylene chloride, chloroform, acetone, ethyl acetate, acetonitrile, N,N-dimethylformamide, dimethyl sulfoxide, water, or a mixed solvent thereof may be used. The mixed solvent is preferably a mixed solvent of 1 to 80% by mass of water and an organic solvent. The organic solvent used in the mixed solvent with water is preferably an aprotic polar solvent, such as tetrahydrofuran, acetone, acetonitrile, N,N-dimethyl formamide, N,N-diethylformamide, or dimethyl sulfoxide, of which a mixed solvent of N,N-dimethyl formamide and water is preferable. An acid or a base may be added to the solvent to adjust to the pH which is suited for formation of a complex.

The concentration of water in the mixed solvent is preferably 1 to 80% by mass, more preferably 3 to 60% by mass, and most preferably 5 to 55% by mass, from the viewpoint of the particle size of the metal complex to be produced. The reaction temperature is preferably −20 to 150° C., and more preferably 50 to 130° C. The reaction time is preferably 1 to 24 hours, and more preferably 2 to 10 hours.

Completion of the reaction can be confirmed by determining the remaining amount of raw materials by gas chromatography or high-performance liquid chromatography. After completion of the reaction, the obtained mixed liquid is subjected to suction filtration to collect a precipitate, which is washed with an organic solvent and then vacuum-dried, for example, at 60 to 100° C. for several hours, thus making it possible to obtain a metal complex to be used in the separating material of the present invention. The metal complex having high crystallinity has high purity and excellent adsorption performance. In order to enhance crystallinity, it is possible to adjust to a suitable pH using an acid or a base.

<Structure of Metal Complex>

Figure 1:
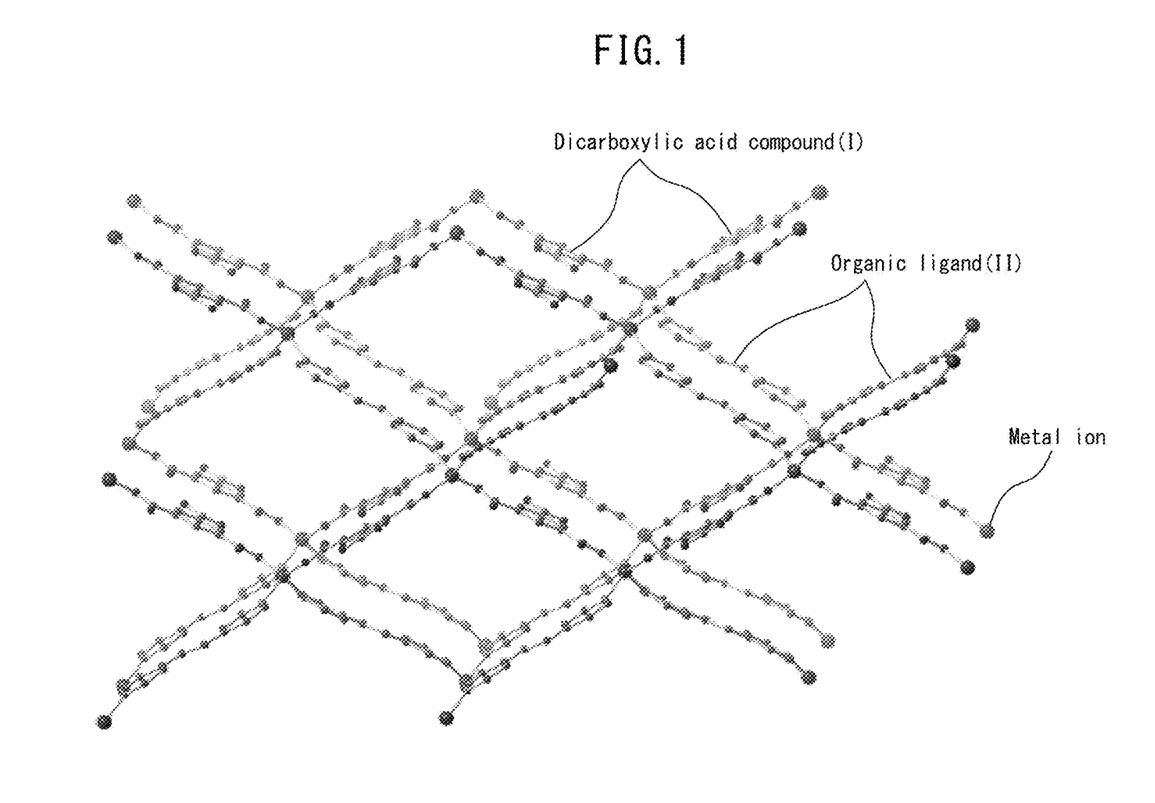
FIG. 1 is a schematic view showing a structure of a pseudo-diamondoid framework.
Figure 2:
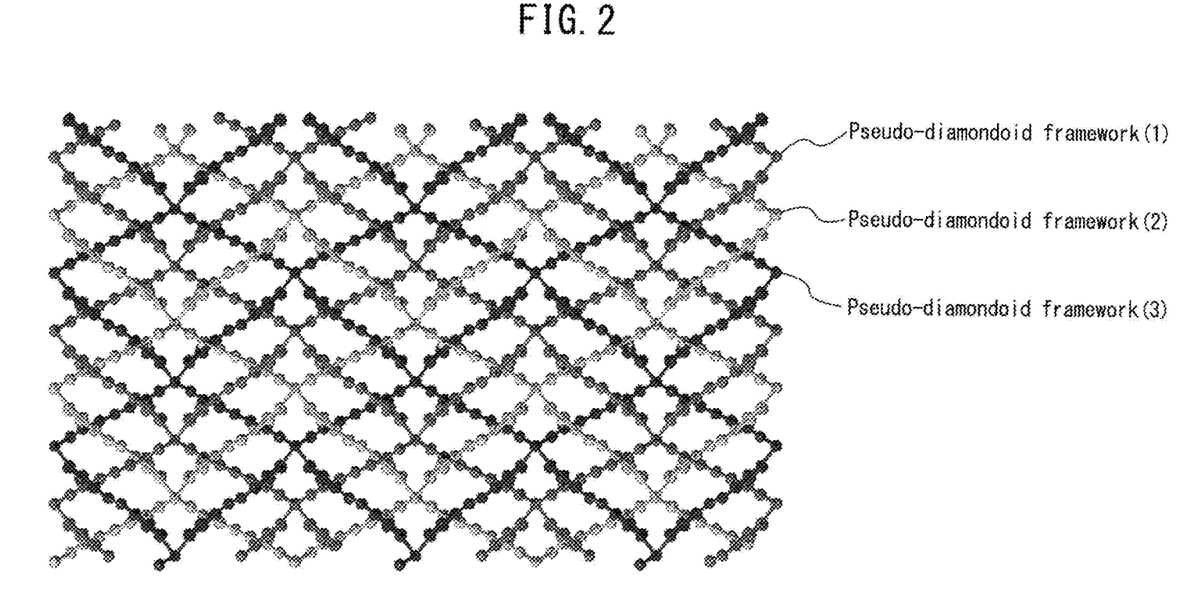
FIG. 2 is a schematic view of a three-dimensional structure in which pseudo-diamondoid frameworks are triply interpenetrated.

The metal complex thus obtained has a three-dimensional structure in which pseudo-diamondoid frameworks are multiply interpenetrated, which is formed by coordination to one metal ion of carboxylate ions of two dicarboxylic acid compounds (I) and two organic ligands (II) capable of bidentate coordination. A structure of a pseudo-diamondoid framework is shown in FIG. 1, and a schematic view of a three-dimensional structure in which pseudo-diamondoid frameworks are triply interpenetrated is shown in FIG. 2. The metal complex preferably has a structure in which pseudo-diamondoid frameworks are triply interpenetrated.

The metal complex used in the separating material of the present invention is usually composed of metal ions, a dicarboxylic acid compound (I) and an organic ligand (II) at a ratio of 1 mol:1 mol:1 mol, and deviation from the ratio is permitted as long as the effects of the present invention can be obtained.

As used herein, "pseudo-diamondoid framework" is defined as a three-dimensional structure like a diamond structure which is formed by coordination to one metal ion of carboxylate ions of two dicarboxylic acid compounds (I) and two organic ligands (II) capable of bidentate coordination.

As used herein, "structure in which pseudo-diamondoid frameworks are multiply interpenetrated" is defined as a three-dimensional integrated structure in which plural pseudo-diamondoid frameworks are interpenetrated in the form of filling pores each other. It is possible to confirm the fact that the metal complex "has a structure in which pseudo-diamondoid frameworks are multiply interpenetrated", for example, by X-ray crystal structural analysis, powder X-ray crystal structural analysis, and the like.

It is possible to change the three-dimensional structure of the metal complex used in the separating material of the present invention even after synthesis. With a change in three-dimensional structure of the metal complex, the structure and size of pores vary. It is presumed that the change in structure depends on type of a substance to be adsorbed, adsorption pressure, adsorption temperature, and the like. Namely, it is considered that, since the degree of structural change varies depending on the substance to be absorbed, in addition to a difference in interaction between the pore surface and the substance to be adsorbed (strength of the interaction is proportional to the magnitude of the Lennard-Jones potential of the substance), the metal complex used in the separating material of the present invention exhibits high selectivity. The present invention can achieve high gas separation performance by controlling the interaction between the pore surface and gas molecules to be adsorbed, and the strength of the interaction between pseudo-diamondoid frameworks interpenetrated each other, using a dicarboxylic acid compound (I) represented by the general formula (I). It is considered that, since the original structure is restored after desorption of the absorbed substance, the structure of the pores also returns to the original structure.

<Separating Method of 1,3-Butadiene>

In the method of separating 1,3-butadiene from a mixed gas containing 1,3-butadiene and a hydrocarbon having 4 carbon atoms other than 1,3-butadiene of the present invention, the mixed gas containing 1,3-butadiene to be separated is brought into contact with the separating material of the present invention to allow the separating material to selectively adsorb 1,3-butadiene, and then 1,3-butadiene adsorbed onto the separating material is desorbed from the separating material, and 1,3-butadiene thus desorbed is collected. The separating material is regenerated by desorption of 1,3-butadiene.

There is no particular limitation on the hydrocarbon having 4 carbon atoms other than 1,3-butadiene contained in the mixed gas. The separating material of the present invention is particularly useful for separating 1,3-butadiene from a mixed gas containing, as the other gas, a hydrocarbon having 4 carbon atoms, for example, butenes, such as isobutene, 1-butene, or 2-butene, butanes, such as normal butane or isobutene, or the like, which are difficult to be separated by a conventional separating material because of having boiling points similar to that of 1,3-butadiene.

In contact between the mixed gas and the separating material, it is desired to select the temperature and pressure conditions under which the separating material adsorbs only the objective 1,3-butadiene.

The separating method comprises an adsorption step of bringing the mixed gas in contact with the separating material of the present invention under the conditions where the separating material can adsorb 1,3-butadiene. The adsorption pressure and adsorption temperature, which are conditions where the separating material can adsorb 1,3-butadiene, can be suitably set according to design of the apparatus, purity required to the product gas, and the like. For example, the partial pressure of 1,3-butadiene in the mixed gas to be introduced in the adsorption step is preferably 70 to 250 kPa, and more preferably 90 to 200 kPa. The adsorption temperature is preferably −5 to 100° C., and more preferably 0 to 50° C.

The separating method may be a pressure swing adsorption method or a temperature swing adsorption method.

Figure 3:
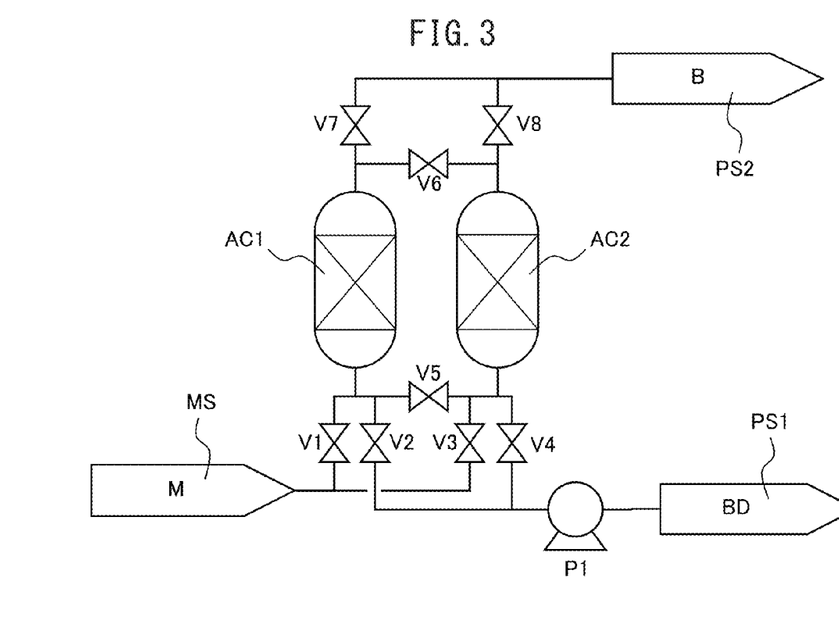
FIG. 3 is a schematic diagram of an apparatus for recovering 1,3-butadiene from a mixed gas using a pressure swing adsorption method.

When the separating method is the pressure swing adsorption method, the method comprises a step (adsorption step) of bringing a mixed gas containing 1,3-butadiene into contact with a separating material to allow the separating material to selectively adsorb only the objective 1,3-butadiene; and a step (regeneration step) of reducing the pressure from the adsorption pressure to a pressure at which the adsorbed 1,3-butadiene can be desorbed from the separating material. The desorption pressure can be suitably set according to design of the apparatus, production efficiency, and the like. For example, the desorption pressure is preferably 0.05 to 50 kPa, and more preferably 0.05 to 30 kPa The pressure swing adsorption method will be specifically described with reference to FIG. 3. Adsorption columns AC1 and AC2 are filled with a separating material of the present invention. A mixed gas (M) containing 1,3-butadiene, butene, butane, and the like is pressurized to about 0.3 MPa by a compressor and supplied to adsorption column AC1 filled with the separating material through valve V1 (abbreviated to "V1", the same shall apply hereinafter) from mixed gas storage tank MS. As is apparent from FIG. 5, when a partial pressure of 1,3-butadiene exceeds 70 kPa, 1,3-butadiene is selectively adsorbed onto the separating material in adsorption column AC1 (adsorption step). Meanwhile, butanes and butenes are not adsorbed, and discharged from adsorption column AC1. As a result, the gas (B) in which butanes and butenes are concentrated is sent to product storage tank PS2 through V7. Next, adsorption column AC1 is suctioned by vacuum pump P1 in the state where V1, V5, V6, and V7 are closed and V2 is opened. As is apparent from FIG. 5, when the pressure is decreased to below 30 kPa, the gas (BD) containing 1,3-butadiene as a main component adsorbed onto the separating material in adsorption column AC1 is desorbed and sent to product storage tank PS1 (desorption step). In the same manner, the adsorption step is completed for adsorption column AC2. After the desorption step of adsorption column AC1 is carried out for a prescribed time, V1, V2, V3, V4, V7, and V8 are closed, and V5 and V6 are opened, and then the mixed gas remaining in adsorption column AC2 is recovered to adsorption column AC1 employing a pressure difference between adsorption column AC1 and adsorption column AC2 (pressure equalizing step). Each product gas can be efficiently obtained without lessening its purity by carrying out the pressure equalizing step. Next, while adsorption column AC2 is suctioned by vacuum pump P1 in the state where V2, V3, V5, V6, and V8 are closed and V4 is opened, the adsorbed gas (BD) containing 1,3-butadiene as a main component is desorbed and sent to product storage tank PS1. To adsorption column AC1, a mixed gas (M) containing 1,3-butadiene is supplied in the state where V2, V3, V5, V6, and V8 are closed and V1 and V7 are opened, and then the adsorption step is carried out again. In adsorption column AC1 and adsorption column AC2, adsorbing and desorbing operations are alternately repeated in a suitably determined cycle by a timer or the like to continuously produce each product gas.

When the separating method is the temperature swing adsorption method, the method comprises a step (adsorption step) of bringing a mixed gas containing 1,3-butadiene into contact with a separating material to allow the separating material to selectively adsorb only the objective 1,3-butadiene; and a step (regeneration step) of raising the temperature from the adsorption temperature to a temperature at which the adsorbed 1,3-butadiene can be desorbed from the separating material. The desorption temperature can be suitably set according to design of the apparatus, production efficiency, and the like. For example, the desorption temperature is preferably 0 to 200° C., and more preferably 20 to 150° C.

When the separating method is the pressure swing adsorption method or the temperature swing adsorption method, a step (adsorption step) of bringing a mixed gas into contact with a separating material, and a step (regeneration step) of changing the pressure or temperature to a pressure or temperature at which 1,3-butadiene can be desorbed from the separating material can be suitably repeated.

Separating methods other than the above-mentioned methods include membrane separation. A separating membrane can be obtained by depositing a metal complex to a surface portion of a porous support, for example, by crystal growth. As the material of the porous support, a composition composed of silica or alumina, such as alumina, silica, mullite, or cordierite, and other components; a porous sintered metal; a porous glass, and the like may be suitably used. Ceramics including other oxides, such as zirconia or magnesia, and carbides and nitrides, such as silicon carbide or silicon nitride, gypsum, cement, or a mixture thereof may also be used. The porosity of the porous support is typically about 30 to 80%, preferably 35 to 70%, and most preferably 40 to 60%. Too small porosity is not preferred since permeability of a fluid, such as gas, deteriorates, while too large porosity is not preferred since the strength of the support decreases. The pore diameter of the porous support is typically 10 to 10,000 nm, and preferably 100 to 10,000 nm. The separating membrane obtained by the crystal growth of a metal complex on a surface portion of a porous support is obtainable by impregnating a porous support in a solution containing a raw material of a metal complex, optionally followed by heating.

A separating membrane can also be obtained by kneading a metal complex of the present invention with a polymer material to disperse the metal complex in the polymer material, and forming the mixture into a film. Examples of the polymer material include polymer materials for gas separating membrane, such as polyvinyl acetate, polyimide, and polydimethylsiloxane.

In the membrane separation, when a mixed gas containing the objective 1,3-butadiene is brought into contact with the separating membrane, the permeability P of each gas in the mixed gas is represented by the product of the solubility S of each gas in the membrane by the diffusion coefficient D thereof in the membrane. Since a gas having higher permeability P selectively permeates through the membrane, such a gas can be separated and recovered from the mixed gas. Therefore, a membrane enabling selective permeation of 1,3-butadiene can be obtained by forming the metal complex having high selectivity of 1,3-butadiene of the present invention into a membrane. For example, when a mixed gas is passed through an inner tube of a double tube, the double tube equipped with a gas impermeable outer tube and the inner tube composed of a separating membrane, 1,3-butadiene selectively permeates through the inner tube and concentrated between the outer tube and the inner tube, and thus the objective 1,3-butadiene can be separated by collecting the gas.

The content of 1,3-butadiene in the mixed gas to be separated varies and significantly depends on a supply source of the mixed gas. The mixed gas contains, in addition to 1,3-butadiene, at least a hydrocarbon, for example, butenes, such as isobutene, 1-butene, or 2-butene, and butanes, such as normal butane or isobutene, and may also contain other hydrocarbons. The mixed gas preferably contains 10 to 99% by volume of 1,3-butadiene based on the total of the volume proportions of 1,3-butadiene and another hydrocarbon (may be a plurality of other hydrocarbons) in the mixed gas. It is more preferable that the proportion of 1,3-butadiene is 20 to 60% by volume.

The separating material of the present invention can be applied to separation of a fraction having 4 carbon atoms (C4 fraction) obtained by naphtha cracking. For example, a mixed gas containing about 40% by volume of 1,3-butadiene is pressurized to not less than 175 kPa, and then passed through an adsorption column filled with the separating material of the present invention for 1 to 10 minutes. After a pressure equalizing step, the pressure is reduced to not greater than 20 kPa by a vacuum pump, whereby 1,3-butadiene adsorbed onto the separating material can be recovered.

EXAMPLES

The present invention will be specifically described by way of Examples, but the present invention is not limited thereto. Analysis and evaluation in the following Examples and Comparative Examples were carried out by the following procedures.
(1) Measurement of Adsorption and Desorption Isothermal Curve Using a high-pressure gas adsorbing apparatus, the measurement was carried out by a volumetric method. A sample was dried at 150° C. under 50 Pa for 6 hours to remove adsorbed water or the like before the measurement. Details of analysis conditions are shown below.
<Analysis Conditions>
Apparatus: BELSORP-18HT, manufactured by BEL Japan, Inc.
Equilibrium waiting time: 500 seconds
(2) Measurement of Powder X-Ray Diffraction Pattern Using X-ray diffractometer: MultiFlex, manufactured by Rigaku Corporation, the measurement was carried out by a symmetric reflection method at a scan rate of 3°/minute within a range of a diffraction angle (2θ) of 3 to 50°. Mercury (ver. 2.3) manufactured by The Cambridge Crystallographic Data Centre was used for conversion into an XRPD diffraction pattern from a single crystal structure.

Synthesis Example 1

Synthesis of [Zn(NO$_2$ip)(bpe)] (Metal Complex 1)

Figure 4:
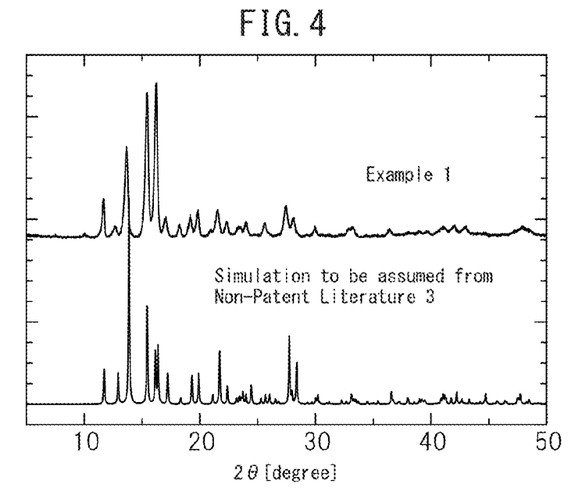
FIG. 4 is a diagram for a comparison between a powder X-ray diffraction pattern of metal complex 1 of Synthesis Example 1, and a powder X-ray diffraction pattern which is predicted from a single crystal structure assumed to take a structure in which pseudo-diamondoid frameworks are multiply interpenetrated.

In a 500 mL recovery flask, 14.4 g (48.4 mmol) of zinc nitrate hexahydrate, 10.5 g (49.7 mmol) of 5-nitroisophthalic acid, 9.11 g (50.0 mmol) of 1,2-di(4-pyridyl)ethene, 180 mL of DMF, and 20 mL of water were charged. The obtained solution was heated under stirring at 120° C. for 6 hours. After cooling to room temperature, the precipitated solid was subjected to suction filtration, washed with DMF and methanol, and then vacuum-dried at 80° C. As a result, 23.3 g (yield: 97%) of the objective metal complex (metal complex 1) was obtained. FIG. 4 shows a comparison between a powder X-ray diffraction pattern which is predicted from a single crystal structure assumed to take a structure in which pseudo-diamondoid frameworks are multiply interpenetrated, and a powder X-ray diffraction pattern of the obtained metal complex 1. As is apparent from FIG. 4, the obtained solid is a metal complex having a structure in which pseudo-diamondoid frameworks are triply interpenetrated as described in Non-Patent Literature 3.

Example 1

Figure 5:
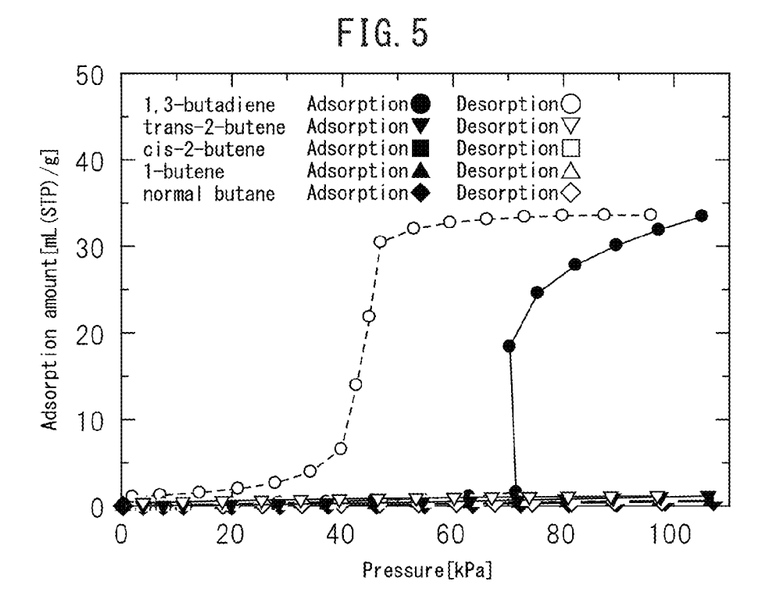
FIG. 5 shows adsorption and desorption isothermal curves of 1,3-butadiene, trans-2-butene, cis-2-butene, 1-butene, and normal butane at 25° C. of a separating material of Example 1.

With respect to metal complex 1 obtained in Synthesis Example 1, adsorption and desorption isothermal curves of 1,3-butadiene, trans-2-butene, cis-2-butene, 1-butene, and normal butane at 25° C. were obtained by the measurement. The results are shown in FIG. 5.

Comparative Example 1

Figure 6:
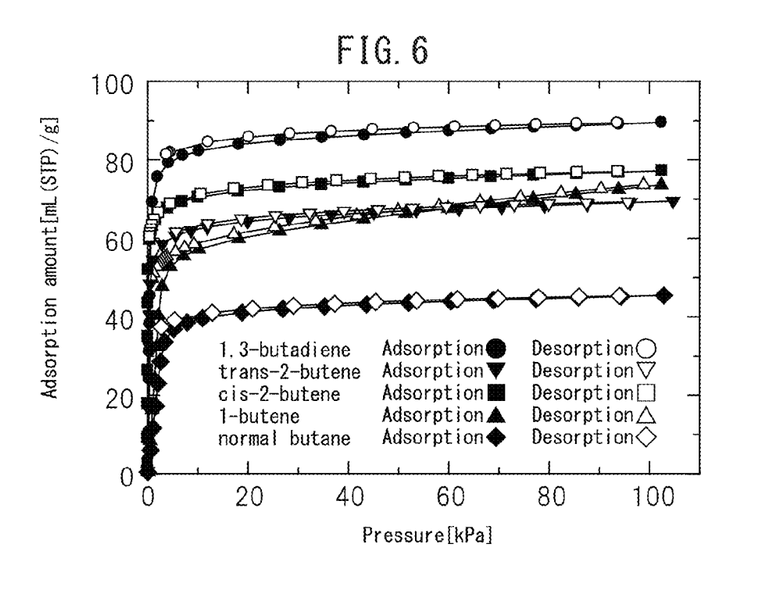
FIG. 6 shows adsorption and desorption isothermal curves of 1,3-butadiene, trans-2-butene, cis-2-butene, 1-butene, and normal butane at 25° C. of a separating material of Comparative Example 1.

With respect to NaY type zeolite (HS-320, manufactured by Wako Pure Chemical Industries, Ltd.) as a typical adsorbing material, adsorption and desorption isothermal curves of 1,3-butadiene, trans-2-butene, cis-2-butene, 1-butene, and normal butane at 25° C. were obtained by the measurement. The results are shown in FIG. 6.

Comparative Example 2

Figure 7:
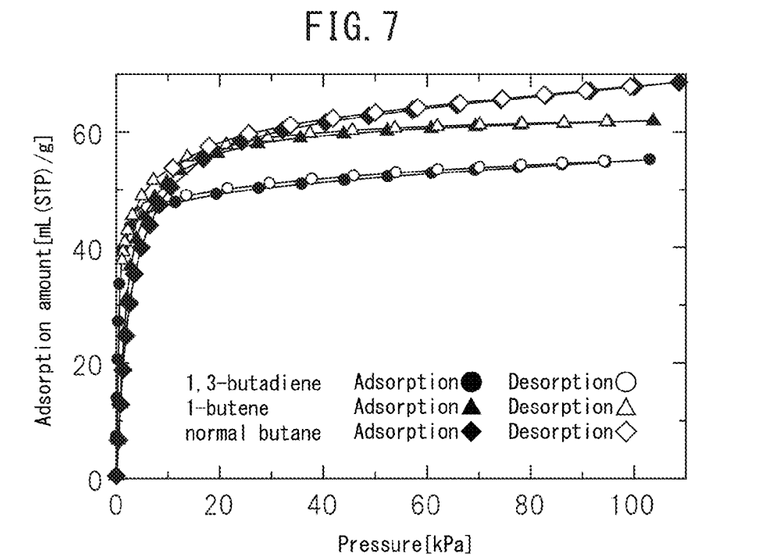
FIG. 7 shows adsorption and desorption isothermal curves of 1,3-butadiene, 1-butene, and normal butane at 25° C. of a separating material of Comparative Example 2.

With respect to Basosiv (trademark) M050 (manufactured by Sigma-Aldrich Japan K.K.) as a typical adsorbing material of a metal complex, adsorption and desorption isothermal curves of 1,3-butadiene, 1-butene, and normal butane at 25° C. were obtained by the measurement. The results are shown in FIG. 7.

As is apparent from FIG. 5, metal complex 1 of Synthesis Example 1 selectively adsorbs 1,3-butadiene under the pressure within a range of 70 to 110 kPa. Therefore, when a mixed gas composed of 1,3-butadiene, 1-butene, and normal butane is supplied under a 1,3-butadiene partial pressure of not less than 70 kPa and brought into contact with the metal complex, only 1,3-butadiene is adsorbed and concentrated. Next, when supply of the mixed gas is stopped and the pressure is decreased to not greater than 20 kPa, 1,3-butadiene is desorbed, whereby a gas in which 1,3-butadiene is concentrated can be obtained. Meanwhile, in FIG. 6 and FIG. 7, selective adsorptivity of 1,3-butadiene is low under the pressure within a range of 0 to 110 kPa. Namely, 1-butene and normal butane are also absorbed, in addition to 1,3-butadiene, thus failing to sufficiently concentrate only 1,3-butadiene.

Example 2

An adsorption tube (measuring 1.0 cm in inner diameter× 20 cm in length) was filled with metal complex 1 (5.3 g) of Synthesis Example 1. Thereafter, in order to activate the metal complex, a filling material was heated at 150° C. before a test, following by evacuation. After cooling to room temperature, a pressure of 0.15 MPaG was created using a pure He gas. Under these conditions, a mixed gas of 1,3-butadiene (67% by volume) and 1-butene (33% by volume) was subsequently allowed to flow into the adsorption tube. The flow rate and composition of a gas flow at an outlet of the adsorption tube were monitored by a flow meter and gas chromatography. The adsorption amount of each gas to the metal complex was calculated based on mass balance. As a result, it was found that the adsorption amount of 1,3-butadiene is 46 mL and that of 1-butene is 4 mL, per 1 g of the metal complex. The results reveal that the concentration of 1,3-butadiene in a C4 mixed gas containing 1,3-butadiene can be concentrated 5 times by using metal complex 1 of Synthesis Example 1 as a separating and adsorbing material.

Synthesis Example 2

Synthesis of [ZnCo(NO$_2$ip)(bpe)] (Metal Complex 2)

In a vessel made of zirconia (45 mL), zinc oxide (0.37 g, 4.5 mmol, 0.9 eq.), cobalt nitrate hexahydrate (0.14 g, 0.5 mmol, 0.1 eq.), 5-nitroisophthalic acid (1.06 g, 5.0 mmol, 1.0 eq.), 1,2-di(4-pyridyl)ethene (0.92 g, 0.50 mmol, 1.0 eq.), distilled water (5 mL), and zirconia ball (3 mmϕ, 25 g) were charged, and then subjected to a wet grinding (using Classic Line (trademark) P-7, manufactured by Fritsch Ltd.) while reacting at normal temperature (25° C.) and 400 rpm for 1 hour. Using Kiriyama-rohto (trademark), the contents were filtered and the precipitated metal complex was washed in turn with ion-exchange water and ethanol, followed by drying. The objective metal complex (metal complex 2) was obtained as a pink solid in the amount of 1.81 g (yield: 79%). As a result of the measurement of a powder X-ray diffraction pattern, it was confirmed that the obtained metal complex 2 is a metal complex having a structure in which pseudo-diamondoid frameworks are triply interpenetrated as shown in FIG. 1 and FIG. 2.

Synthesis Example 3

Synthesis of [ZnFe(NO$_2$ip)(bpe)] (Metal Complex 3)

In a vessel made of zirconia (45 mL), zinc oxide (0.37 g, 4.5 mmol, 0.9 eq.), ammonium iron nitrate hexahydrate (0.23 g, 0.5 mmol, 0.1 eq.), 5-nitroisophthalic acid (1.06 g, 5.0 mmol, 1.0 eq.), 1,2-di(4-pyridyl)ethene (0.92 g, 0.50 mmol, 1.0 eq.), distilled water (5 mL), and zirconia balls (3 mmϕ, 25 g) were charged, and then subjected to a wet grinding (using Classic Line (trademark) P-7, manufactured by Fritsch Ltd.) while reacting at normal temperature (25° C.) and 400 rpm for 1 hour. Using Kiriyama-rohto (trademark), the contents were filtered and the precipitated metal complex was washed in turn with ion-exchange water and ethanol, followed by drying. The objective metal complex (metal complex 3) was obtained as a brown solid in the amount of 1.98 g (yield: 84%). As a result of the measurement of a powder X-ray diffraction pattern, it was confirmed that the obtained metal complex 3 is a metal complex having a structure in which pseudo-diamondoid frameworks are triply interpenetrated as shown in FIG. 1 and FIG. 2.

Synthesis Example 4

Synthesis of [ZnCu(NO$_2$ip) (bpe)] (Metal Complex 4)

In a vessel made of zirconia (45 mL), zinc oxide (0.37 g, 4.5 mmol, 0.9 eq.), copper nitrate trihydrate (0.15 g, 0.5 mmol, 0.1 eq.), 5-nitroisophthalic acid (1.07 g, 5.0 mmol, 1.0 eq.), 1,2-di(4-pyridyl)ethene (0.93 g, 0.50 mmol, 1.0 eq.), distilled water (5 mL), and zirconia balls (3 mmϕ, 25 g) were charged, and then subjected to a wet grinding (using Classic Line (trademark) P-7, manufactured by Fritsch Ltd.) while reacting at normal temperature (25° C.) and 400 rpm for 1 hour. Using Kiriyama-rohto (trademark), the contents were filtered and the precipitated metal complex was washed in turn with ion-exchange water and ethanol, followed by drying. The objective metal complex (metal complex 4) was obtained as a blue solid in the amount of 1.92 g (yield: 81%). As a result of the measurement of a powder X-ray diffraction pattern, it was confirmed that the obtained metal complex 4 is a metal complex having a structure in which pseudo-diamondoid frameworks are triply interpenetrated as shown in FIG. 1 and FIG. 2.

Examples 3 to 5

Figure 8:
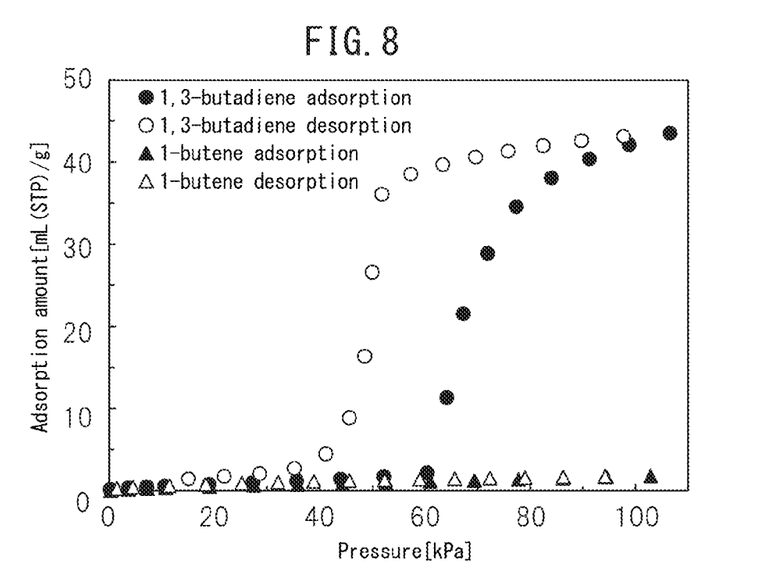
FIG. 8 shows adsorption and desorption isothermal curves of 1,3-butadiene and 1-butene at 25° C. of a separating material of Example 3.
Figure 9:
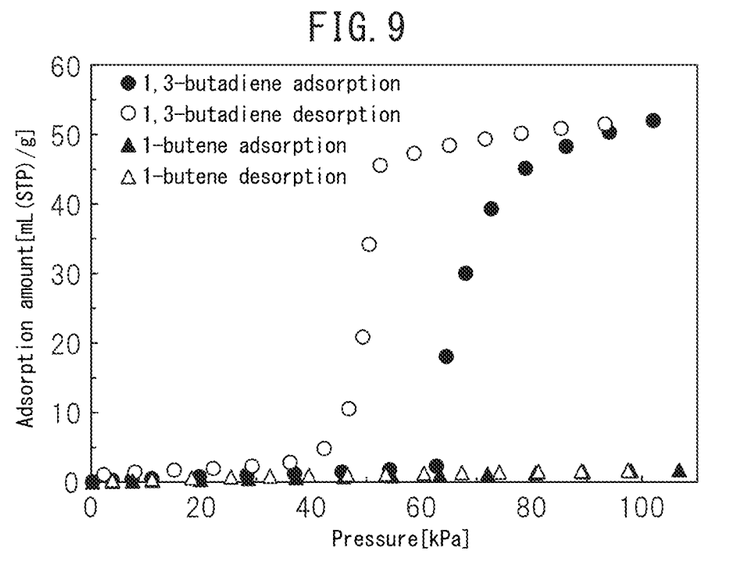
FIG. 9 shows adsorption and desorption isothermal curves of 1,3-butadiene and 1-butene at 25° C. of a separating material of Example 4.
Figure 10:
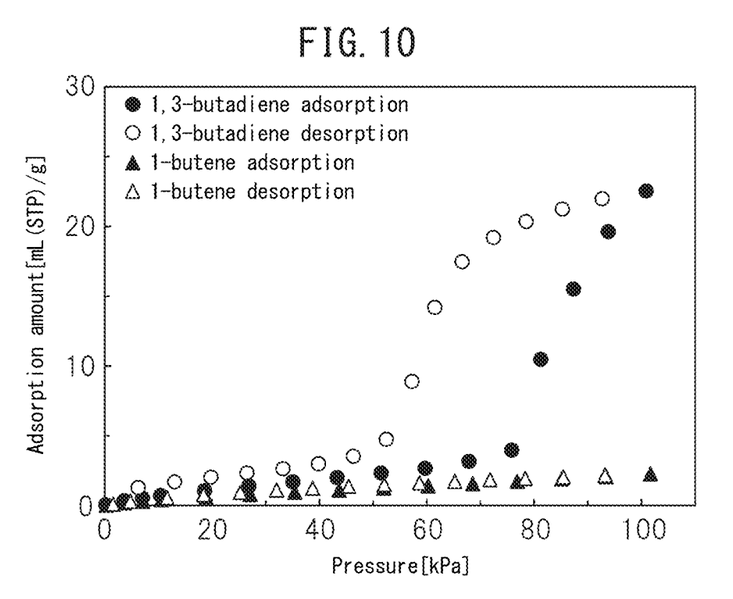
FIG. 10 shows adsorption and desorption isothermal curves of 1,3-butadiene and 1-butene at 25° C. of a separating material of Example 5.

With respect to the respective metal complexes 2 to 4 obtained in Synthesis Examples 2 to 4, adsorption and desorption isothermal curves of 1,3-butadiene and 1-butene at 25° C. were obtained by the measurement. The results are shown in FIGS. 8 to 10.

REFERENCE SIGNS LIST

MS Mixed gas storage tank
PS1, PS2 Product storage tank
AC1, AC2 Adsorption column
P1 Vacuum pump
V1 to V8 Valve
M Mixed gas
B Gas containing concentrated butanes and butenes
BD Gas containing 1,3-butadiene as a main component

The invention claimed is:
1. A 1,3-butadiene-separating material capable of selectively adsorbing 1,3-butadiene from a mixed gas containing 1,3-butadiene and a hydrocarbon having 4 carbon atoms other than 1,3-butadiene, comprising a metal complex having a structure in which pseudo-diamondoid frameworks are multiply interpenetrated, the metal complex being composed of
a dicarboxylic acid compound (I) represented by the following general formula (I):

(I)

wherein R¹, R², R³, and R⁴ may be the same or different and represent a hydrogen atom, an alkyl group having 1 to 4 carbon atoms which may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkylamino group having 1 to 4 carbon atoms, a dialkylamino group having 2 to 4 carbon atoms, an acylamino group having 2 to 4 carbon atoms, or a halogen atom;

ions of at least one metal selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium; and an organic ligand (II), which is capable of bidentate coordination to the metal ions, represented by the following general formula (II):

(II)

wherein X represents —CH₂—, —CH₂—CH₂—, —CH=CH—, —C≡C—, —O—, —S—, —S—S—, —N=N—, or —NHCO—, and R⁵, R⁶, R⁷, R⁸, R⁹, R¹⁰, R¹¹, and R¹² may be the same or different and represent a hydrogen atom, an alkyl group having 1 to 4 carbon atoms which may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkylamino group having 1 to 4 carbon atoms, a dialkylamino group having 2 to 4 carbon atoms, an acylamino group having 2 to 4 carbon atoms, or a halogen atom.

2. The 1,3-butadiene-separating material according to claim 1, wherein the ions of the metal are zinc ions.

3. The 1,3-butadiene-separating material according to claim 1, wherein the organic ligand (II) represented by the general formula (II) is 1,2-di(4-pyridyl)ethene in which all of R⁵, R⁶, R⁷, R⁸, R⁹, R¹⁰, R¹¹, and R¹² are hydrogen atoms, and X is —CH=CH—.

4. The 1,3-butadiene-separating material according to claim 1, wherein, in the dicarboxylic acid compound (I) represented by the general formula (I), R¹, R³, and R⁴ are hydrogen atoms, and R² is a hydrogen atom, a methyl group, or a nitro group.

5. The 1,3-butadiene-separating material according to claim 1, wherein the metal complex has a structure in which pseudo-diamondoid frameworks are triply interpenetrated.

6. The 1,3-butadiene-separating material according to claim 1, wherein the hydrocarbon having 4 carbon atoms other than 1,3-butadiene is butene or butane.

7. A separating method of 1,3-butadiene in which 1,3-butadiene is separated from a mixed gas, the method comprising an adsorption step of bringing the mixed gas containing 1,3-butadiene and a hydrocarbon having 4 carbon atoms other than 1,3-butadiene into contact with a separating material to allow the separating material to selectively adsorb 1,3-butadiene; and a regeneration step of desorbing 1,3-butadiene adsorbed onto the separating material from the separating material, and collecting 1,3-butadiene thus desorbed; wherein the separating material is the 1,3-butadiene-separating material according to claim 1.

8. The separating method of 1,3-butadiene according to claim 7, wherein the hydrocarbon having 4 carbon atoms other than 1,3-butadiene is butene or butane.

9. The separating method of 1,3-butadiene according to claim 7, wherein the separating method is a pressure swing adsorption method.

10. The separating method of 1,3-butadiene according to claim 7, wherein the separating method is a temperature swing adsorption method.

11. A 1,3-butadiene-separating membrane comprising a porous support, and the 1,3-butadiene-separating material according to claim 1 deposited on a surface portion of the porous support.

12. A 1,3-butadiene-separating membrane comprising a polymer material, and the 1,3-butadiene-separating material according to claim 1 kneaded with and dispersed in the polymer material.

13. A separating method of 1,3-butadiene in which a gas having a higher 1,3-butadiene concentration than that of a mixed gas is obtained, the method comprising bringing a mixed gas containing 1,3-butadiene and a hydrocarbon having 4 carbon atoms other than 1,3-butadiene into contact with a separating membrane to selectively permeate 1,3-butadiene through the separating membrane, wherein the separating membrane is the 1,3-butadiene-separating membrane according to claim 11.

14. The 1,3-butadiene-separating material according to claim 2, wherein the organic ligand (II) represented by the general formula (II) is 1,2-di(4-pyridyl)ethene in which all of R⁵, R⁶, R⁷, R⁸, R⁹, R¹⁰, R¹¹, and R¹² are hydrogen atoms, and X is —CH=CH—.

* * * * *